United States Patent
Lin

(10) Patent No.: US 7,119,166 B2
(45) Date of Patent: *Oct. 10, 2006

(54) UNIVERSAL PROCEDURE FOR REFOLDING RECOMBINANT PROTEINS

(75) Inventor: Xinli Lin, Piedmont, CA (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 216 days.

This patent is subject to a terminal disclaimer.

(21) Appl. No.: 10/420,044

(22) Filed: Apr. 17, 2003

(65) Prior Publication Data

US 2003/0199676 A1    Oct. 23, 2003

Related U.S. Application Data

(63) Continuation of application No. 09/752,878, filed on Dec. 28, 2000, now Pat. No. 6,583,268.

(60) Provisional application No. 60/210,306, filed on Jun. 8, 2000, provisional application No. 60/210,292, filed on Jun. 8, 2000, provisional application No. 60/178,368, filed on Jan. 27, 2000, provisional application No. 60/177,836, filed on Jan. 25, 2000.

(51) Int. Cl.
*C07K 14/00* (2006.01)
*C12P 21/06* (2006.01)

(52) U.S. Cl. ............... 530/350; 530/412; 530/417; 530/427; 435/69.1; 435/252.3; 435/320.1

(58) Field of Classification Search ........ 530/350, 530/412, 417, 427; 435/69.1, 70.1, 252.1, 435/252, 320.1, 252.3
See application file for complete search history.

(56) References Cited

U.S. PATENT DOCUMENTS

| 4,518,526 | A | 5/1985 | Olson |
|---|---|---|---|
| 6,545,127 | B1 | 4/2003 | Tang et al. |
| 6,583,268 | B1 | 6/2003 | Lin |
| 2001/0044521 | A1 | 11/2001 | Lin |
| 2002/0049303 | A1 | 4/2002 | Tang et al. |
| 2002/0115600 | A1 | 8/2002 | Koelsch et al. |
| 2002/0164760 | A1 | 11/2002 | Lin et al. |
| 2004/0167075 | A1 | 8/2004 | Tang et al. |
| 2004/0220079 | A1 | 11/2004 | Koelsch et al. |
| 2004/0265298 | A1 | 12/2004 | Lin |

FOREIGN PATENT DOCUMENTS

| WO | WO 01/00663 A | 1/2001 |
|---|---|---|
| WO | WO-01/55174 A2 | 8/2001 |
| WO | WO-01/55174 A3 | 8/2001 |
| WO | WO-2004/094344 A2 | 11/2004 |
| WO | WO-2005/058930 A2 | 6/2005 |

OTHER PUBLICATIONS

Chen, "Recombinant rhizopuspepsingen," J Biol Chem 266(18):11718-11725 (1991).
Cheng, et al., "High-level synthesis of recombinant HIV-1 protease and the recovery of active enzyme from inclusion bodies," Gene 87:243-248 (1990).
Ermolieff, et al., "Kinetic properties of saquinavir-resistant mutants of human immunodeficiency virus type 1 protease and their implications in drug resistance in vivo," Biochemistry 36(40):12364-12370 (1997).
Fusek, et al., "Enzymic properties of thermopsin," J Biol Chem 265(3):1496-1501 (1990).
Ghosh, et al., "Design of potent inhibitors for human brain memapsin 2 (□-secretase)," J Am Chem Soc 122:3522-3523 (2000).
Huxtable, et al., "Renaturation of 1-aminocyclopropane-1-carboxylate synthesis expressed in *E. coli.* in the form of inclusion bodies into a dimeric and catalytically active enzyme," Protein Expression and Purification 12(3):305-314 (1998).
Kelley & Winkler, "Folding of eukaryotic proteins produced in *E. coli,*" Genetic Engineering 12:1-19 (1990).

(Continued)

*Primary Examiner*—Jon Weber
*Assistant Examiner*—Rita Mitra
(74) *Attorney, Agent, or Firm*—Morrison & Foerster LLP

(57) ABSTRACT

A universal folding method that has been demonstrated to be effective in refolding a variety of very different proteins expressed in bacteria as inclusion bodies has been developed. Representative proteins that can be dissolved and refolded in biologically active form, with the native structure, are shown in Table I. The method has two key steps to unfold and then refold the proteins expressed in the inclusion bodies. The first step is to raise the pH of the protein solution in the presence of denaturing agents to pH greater than 9, preferably 10. The protein solution may be maintained at the elevated pH for a period of up to about 24 hours, or the pH immediately decreased slowly, in increments of about 0.2 pH units/24 hours, until the solution reaches a pH of about 8.0, or both steps used. In the preferred embodiment, purified inclusion bodies are dissolved in 8 M urea, 0.1 M Tris, 1 mM glycine, 1 mM EDTA, 10 mM beta-mercaptoethanol, 10 mM dithiothreitol (DTT), 1 mM reduced glutathione (GSH), 0.1 mM oxidized glutathione (GSSG), pH 10. The absorbance at 280 nm (OD280) of the protein solution is 5.0. This solution is rapidly diluted into 20 volumes of 20 mM Tris base. The resulting solution is adjusted to pH 9.0 with 1 M HCl and is kept at 4° C. for 24 hr. The pH is adjusted to pH 8.8 and the solution is kept at 4° C. for another 24 hrs. This process is repeated until the pH is adjusted to 8.0. After 24 hr at pH 8.0, the refolded proteins can be concentrated by ultrafiltration and applied to a gel filtration column for purification.

25 Claims, No Drawings

OTHER PUBLICATIONS

Koelsch, et al., "Enzymic characteristics of secreted aspartic proteases of *Candida albicans*," Biochemica et Biophysica Acta 1480:117-131 (2000).

Lin & Tang, "Purification, characterization, and gene cloning of thermopsin, a thermostable acid protease from Sulfolobus acidocaldarius," J Biol Chem 265(3):1490-1495 (1990).

Lin, "Construction of new retroviral producer cells from adenoviral and retroviral vectors," Gene Therapy 5:1251-1258 (1998).

Lin, et al., "Conformational instability of the N- and C- terminal lobes of porcine pepsin in neutral and alkaline solutions," Protein Science 2:1383-1390 (1993).

Lin, et al., "Effect of point mutations on the kinetic and the inhibition of human immunodefiency virus type 1 protease: Relationship to drug resistance," Biochemistry 34(4):1143-1152 (1995).

Lin, et al., "Enzymatic activities of two-chain pepsinogen, two-chain pepsin, and the amino-terminal lobe of pepsinogen," J Biol Chem 267(24):17257-17263 (1992).

Lin, et al., "Heterologous expression of thermopsin, a heat-stable acid proteinase," Enzyme Microb Technol 14:696-701 (1992).

Lin, et al., "Human aspartic protease memapsin 2 cleaves the beta-secretase site of beta-amyloid precursor protein," Proc. Natl. Acad. Sci USA 97(4):1456-1460 (2000).

Lin, et al., "Intracellular diversion of glycoprotein GP160 of human immunodeficiency virus to lysosomes as a strategy of AIDS gene therapy," FASEB Journal 7:1070-1080 (1993).

Lin, et al., "pH dependence of kinetic parameters of pepsin, rhizopuspepsin, and their active-site hydrogen bond mutants," J Biol Chem 267(26):18413-18418 (1992).

Lin, et al., "Recombinant canditropsin, an extracellular aspartic protease from yeast *Candida tropicals*," J Biol Chem 268(27):20143-20147 (1993).

Lin, et al., "Relationships of human immunodeficiency virus protease with eukaryotic aspartic protease," Methods in Enzymology 241:195-224 (1994).

Lin, et al., "Synthesis, purification, and active site mutagenesis of recombinant porcine pepsinogen," J Biol Chem 264(8):4482-4489 (1989).

Reed, et al., "Alteration of glycosylation renders HIV sensitive to inactivation by normal human serum," J Immunology 159:4359-4361 (1997).

Roswell, "Lysosome-associated membrane protein-1-mediated targeting of the HIV-1 envelope protein to an endosomal/lysosomal compartment enhances its presentation to MHC Class II-restricted T cells," J Immunology 155:1818-1828 (1995).

Tang & Lin, "A new anti-HIV gene therapy strategy—Diversion of gp160 to lysosomes," International Antiviral News 2(2):19-20 (1994).

Tang & Lin, "Engineering aspartic proteases to probe structure and function relationships," Current Opinion in Biotechnology 5:422-427 (1994).

Tang, et al., "Understanding HIV protease: Can it be translated into effective therapy against AIDS?" Scand J Clin Lab Invest Suppl 210:127-35 (1992).

Tichy, et al., "Improved procedure for high-yield recovery of enzymatically active recombinant calf chymosin from *E. coli* inclusion bodies," Protein Expression and Purification 4(1):59-63 (1993).

Wang, et al., "Crystal structure of the catalytic domain of human plasmin complexed with streptokinase," Science 281:1662-1665 (1998).

Wang, et al., "Human plasminogen catalytic domain undergoes an unusual conformational change upon activation," J Mol. Biol 295:903-914 (2000).

Wei, et al., "Oxidative refolding of recombinant prochymosin," Biochem. J. 340:345-351 (1999).

Fischer, B. et al. (1993). "Isolation, Renaturation, and Formation of Disulfide Bonds of Eukaryotic Proteins Expressed in *Escherichia coli* as Inclusion Bodies," *Biotechnology and Bioengineering* 41:3-13.

Lin, X. U.S. Appl. No. 11/011,406 filed Dec. 13, 2004.

US 7,119,166 B2

UNIVERSAL PROCEDURE FOR REFOLDING RECOMBINANT PROTEINS

This application is a continuation of U.S. Ser. No. 09/752,878, filed Dec. 28, 2000, now U.S. Pat. No. 6,583,268, which claims the priority benefit of provisional patent applications U.S. Ser. No. 60/177,836 filed Jan. 25, 2000; U.S. Ser. No. 60/178,368 filed Jan. 27, 2000; U.S. Ser. No. 60/210,292 filed Jun. 8, 2000; and U.S. Ser. No. 60/2 10,306 filed Jun. 8, 2000.

BACKGROUND OF THE INVENTION

The present invention is generally in the field of methods for manufacture of recombinant proteins, and especially in the field of refolding of recombinant proteins expressed in the inclusion bodies of procaryotic expression systems such as E. coli.

Expression of recombinant proteins with natural biological activity and structure, referred to as "proteomics", becomes increasingly important with the completion of genomic sequencing for several organisms and the near completion of human genome sequencing. One aspect of proteomics is to express large amounts of protein for structural and functional studies, as well as for commercial applications. The least expensive and most efficient way to express recombinant proteins is to express the proteins in E. coli. Proteins are expressed either intracellularly or secreted into the periplasmic spaces. In the former case, the proteins are often deposited in inclusion bodies, especially if the protein has disulfide bonds.

However, one of the problems in expressing mammalian proteins in E. coli is that most of the expressed proteins form insoluble inclusion bodies. While this problem can be circumvented by using various mammalian or insect expression systems, growing E. coli is faster and less expensive compared to mammalian and insect cultures. Moreover, some proteins are toxic to the host when expressed in their native forms, thus expression as insoluble inclusion bodies is the only way to obtain large quantities of recombinant proteins. Importantly, high levels of expression can be achieved for most proteins. 400 to 600 mg of inclusion bodies per liter of bacterial culture can routinely be achieved, with up to 9,700 mg/L having been reported using this method (Jeong K L; Lee S Y, 1999. Appl. Environ. Microbiol 65:3027–32). Inclusion bodies can be easily purified to greater than 90% with a simple freeze/thaw and detergent washing procedure.

Inclusion bodies appear as dense cytoplasmic granules when the cells are observed under a light microscope. Typically, the cells will be lysed by mechanical disruption of the cells, followed by centrifugation for 30 min at 4700 g. Inclusion bodies will sediment at low g forces and can be separated from many other intracellular proteins. Further purification can be done by washing the pellet with the buffer used during the cell disruption, or by centrifuging the resuspended pellet in 40–50% glycerol.

Many extracellular proteins of eukaryotes contain disulfide bonds. Proteins having multiple disulfide bonds may form non-native disulfide bonds during folding from the reduced species. Further folding is then blocked unless the incorrect disulfide bond is cleaved by reduction with an external thiol or by attack from a protein thiol. Eukaryotic organisms that secrete disulfide containing proteins also machinery for ensuring proper disulfide bond formation. A distinct disadvantage of expression of recombinant proteins in prokaryotes as inclusion bodies is that the proteins are not obtained in their native state, and typically are not functionally active. A variety of methods have been used to re-solubilize the proteins and refold them to reform active protein. Dissolution of the pelleted recombinant protein usually requires the use of denaturants such as 7 M guanidine hydrochloride or 8 M urea. The amount of aggregation may continue to increase with time if the protein is allowed to remain in the denaturant (Kelley and Winkler, "Folding of Eukaryotic Proteins Produced in Escherichia coli" Genetic Engineering 12, 1–19 at p. 6 (1990)). Removal of the denaturant from the solubilized inclusion bodies by dialysis or desalting columns will cause the protein to precipitate under conditions where the native protein needs to be refolded. A misfolded protein solution can also have a very low specific activity in biological assays.

Although there are many reports of expression and refolding of various proteins in E. coli as inclusion bodies, one of the misconceptions in protein refolding is that a unique refolding method has to be developed for each individual protein (see Kelley and Winkler at p. 6). Another misconception is that most of the mammalian proteins cannot be refolded from inclusion bodies. (for review, see: Rudolph R., Lilie H., 1996. FASEB J 10:49–56; Lilie H, Schwarz E, Rudolph R. 1998. Curr Opin Biotechnol 9:497–501). Because published works are mostly "success" stories in refolding inclusion bodies from E. coli, it is impossible to get a general idea about what percentage of mammalian proteins can be purified using this procedure.

There are probably more refolding methods than refolded proteins reported in the literature (for review, see: Rudolph R., Lilie, H. 1996, FASEB J 10:49–56; Lilie, H., Schwarz, E., Rudolph, R. 1998, Curr. Opin. Biotechnol. 9:497–501). Different chaperones, detergents, and chaotrophs have been used to help refolding. In addition, pH, ionic strength, temperature, buffer formulation, and reducing/oxidation reagents can all effect refolding. It would be prohibitive to test all these conditions for refolding large amounts of proteins, as required for studies in proteomics or structural genomics.

A single simplified procedure to refold most of the proteins that are expressed in recombinant systems, especially those which form inclusion bodies in systems such as E. coli, is therefore needed.

It is therefore an object of the present invention to provide a "universal" method for refolding of proteins, especially recombinant proteins, especially recombinant proteins present in inclusion bodies in bacterial hosts.

SUMMARY OF THE INVENTION

A universal folding method that has been demonstrated to be effective in refolding a variety of very different proteins expressed in bacteria as inclusion bodies has been developed. Representative proteins that can be dissolved and refolded in biologically active form, with the native structure, are shown in Table I. The method has two key steps to unfold and then refold the proteins expressed in the inclusion bodies. The first step is to raise the pH of the protein solution in the presence of denaturing agents to pH greater than 9, preferably 10. The protein solution may be maintained at the elevated pH for a period of up to about 24 hours, or the pH immediately decreased slowly, in increments of about 0.2 pH units/24 hours, until the solution reaches a pH of about 8.0, or both steps used. In the preferred embodiment, purified inclusion bodies are dissolved in 8 M urea, 0.1 M Tris, 1 mM glycine, 1 mM EDTA, 10 mM beta-mercaptoethanol, 10 mM dithiothreitol (DTT), 1 mM reduced glutathione (GSH), 0.1 mM oxidized glutathione (GSSG), pH 10. The absorbance at 280 nm (OD280) of the protein solution is 5.0. This solution is rapidly diluted into 20 volumes of 20 mM Tris base. The resulting solution is adjusted to pH 9.0 with 1 M HCl and is kept at 4° C. for 24 hr. The pH is adjusted to pH 8.8 and the solution is kept at 4° C. for another 24 hrs. This process is repeated until the pH is adjusted to 8.0. After 24 hr at pH 8.0, the refolded proteins can be concentrated by ultrafiltration and applied to a gel filtration column for purification.

DETAILED DESCRIPTION OF THE INVENTION

Expression of Recombinant Proteins

Recombinant proteins are typically expressed in a suitable host, for example, a prokaryotic expression system such as *E. coli* or other type of bacteria, using a standard expression vector like a plasmid, bacteriophage or even naked DNA, and the protein expressed from the plasmid or DNA integrated the host chromosome. Suitable bacterial strains are commercially available or can be obtained from the American Type Culture Collection (ATCC), 10801 University Boulevard, Manassas, Va. 20110-2209.

Suitable vectors can be obtained from any number of sources, including the ATCC. These need a promoter to insure that the DNA is expressed in the host, and may include other regulatory sequences. The vector may also include means for detection, such as an antibiotic resistance marker, green fluorescent protein tag, or antigen tag to facilitate in purification of the recombinant protein.

Once the DNA encoding the protein to be purified is introduced into the host, the host is cultured under appropriate conditions until sufficient amounts of recombinant protein are obtained.

Refolding/Purification Methods

Once the protein has been expressed in the maximum amount, it must be separated and purified from the bacterial host. The protein is isolated generally y lysing the cells, for example, by suspending in detergent, adding lysozyme, and then freezing (for example, by suspending cells in 20 ml of TN/1% Triton™ X-100, adding 10 mg lysozyme and freezing at −20° C. overnight), thawing and adding DNAase to degrade all of the bacterial DNA, then washing the resulting precipitate in a buffered solution. The precipitate is then dissolved in an appropriate solution as discussed below, for refolding.

The isolated protein is then refolded. There are several critical aspects of an universal refolding method.

(i) High pH refolding. Most published procedures refold proteins using reducing chaotrophs (such as 8 M urea) at a physiological pH, usually pH 7.4 to 8.0. This usually produces large quantities of precipitation or aggregation, making refolding either impossible or with a very low yield. It has been found that some proteins cannot be refolded at physiological pH, but can be refolded when initial refolding pH is high (at least pH 9.0, although higher pH, such as pH 10, may be desirable). This strategy was initially inspired by the fact that pepsinogen can be reversibly denatured/renatured between pH 8.0 and 9.0. It is postulated that at high pH (such as pH 9.0), proteins can obtain some secondary structures, allowing it to be refolded more efficiently when acidity of the refolding solution is lowered to the biological pH. Later it was found that even for the proteins that could be refolded at a physiological pH, high pH refolding resulted in a better yield. In addition, high pH refolding is an excellent method for preventing initial large scale precipitation.

(ii) Non-denaturing chaotroph concentration. It has been shown in several labs that non-denaturing concentrations of chaotrophic reagents, such as 0.5 to 1.0 M of urea, guanidine hydrochloride, and L-arginine, can be used to assist refolding and stabilize refolded proteins (Rudolph et al. 1996, *FASEB J* 10:49–56). The preferred concentration of chaotrophic reagents is 0.4 M, although the concentration may range from 0 to 4 M. A moderate concentration of urea in the refolding/purification procedures has not been found to have a denaturing effect on proteins.

(iii) Reducing/oxidation reagents. Inclusion bodies for mammalian proteins containing disulfide bonds need to be dissolved in the presence of reducing reagents. Representative reducing agents include beta-mercaptoethanol, in a range of from 0.1 mM to 100 mM, preferably 10 mM; DTT, in a range of from 0.1 mM to 10 mM, preferably 10 mM; reduced glutathione (GSH), in a range from 0.1 mM to 10 mM, preferably 1 mM; and oxidized glutathione (GSSG), in a range from 0.1 mM to 10 mM, preferably mM. Beta-mercaptoethanol is a preferred reducing reagent. In addition, dithiothreitol and/or reduced/oxidized glutathione (GSH, GSSG) can also be included to facilitate "oxido-shuffling" of wrongly folded, intermediate disulfide bonds.

(iv) pH control It is important that the protein solution remain at an elevated condition long enough to refold the protein. This is preferably achieved by decreasing the pH slowly, in 0.2 pH unit increments per 24 hours. In this method, the protein solution is adjusted to a high pH, preferably at least 9.0 or higher, to 10 or less preferably 11. The protein is preferably maintained at each pH for at least 24 hours, although comparable effects can be achieved with shorter periods of time, for example, for a period of three, six, nine, twelve, eighteen or twenty hours, most preferably at least twelve hours. The pH can be adjusted by addition of an acid or by dialysis or dilution into a lower pH. Addition of the acid is preferred.

The four conditions discussed above are considered the most essential aspects of the basic protocol for the "universal" refolding procedure.

TABLE I

Expression, refolding, and purification of different proteins from *E. coli*

| Name | From | Organism | Refold | Purification | Ref. |
|---|---|---|---|---|---|
| Pepsinogen | Full-length | Porcine | Yes | Yes | Lin, et al, 1989 |
| Pepsinogen | N and C Domain | Porcine | Yes | Yes | Lin, et al, 1992<br>Lin, et al, 1993 |
| Rhizopus-Pepsinogen | full-length | Fungus | Yes | Yes | Chen, et al, 1991<br>Lin, et al, 1992 |
| Thermopsin | full-length | Archae | No | No | None |
| Thermopsin | fusion | Archae | Yes | Partial | Lin, Liu, Tang, 92 |
| Cathepsin D | full-length | human | No | No | None<br>low yield |
| Pregnancy Specific Ant | full-length | Bovine Ovine | No | No | None |
| HIV protease | full-length | HIV | Yes | Yes | Lin, et al, 1995<br>Ermolief, et al, 97 |
| SAP | full-length | Yeast | Yes | Yes | Lin, et al, 1993<br>Koelsch, et al, 98 |
| Streptokinase | full-length | bacteria | Yes | Yes | Wang, et al, 1998 |
| Plasminogen | cat-domain | human | Yes | Yes | Wang, et al, 2000 |
| Cadosin A | full-length | plant | Yes | Yes | Faro, et al, 1999 |
| Napsin 1 | full-length | human | No | No | Koelsch, et al, 00 |
| Memapsin 2 | full-length | human | Yes | Yes | Lin, et al, 2000 |
| Memapsin 1 | full-length | human | Yes | Yes | |
| PreS | partial | HBV | Yes | Yes | |
| unc-76 | full-length | *C. elegans* | Yes | Yes | |
| odc-1 | full-length | *C. elegans* | Yes | Yes | |
| ceh-10 | full-length | *C. elegans* | Yes | Yes | |
| ppp-1 | full-length | *C. elegans* | No | No | |

References for Table 1:

Lin, X, Wong, R.N.S., and Tang, J. (1989) "Synthesis, purification, and active site mutagenesis of recombinant porcine pepsinogen". J. Biol. Chem. 264: 4482–4489.

Lin, X.L., Lin, Y.-Z., Koelsch, G., Gustchina, A., Wlodawer, A., and Tang, J. (1992) "Enzymic activities of two-chain pepsinogen, two-chain pepsin, and the amino-terminal lobe of pepsinogen". J. Biol. Chem. 267: 17257–17263.

Lin, X., Loy, J.A., Sussman, F., and Tang, J. (1993) "Conformational instability of the N- and C-terminal lobes of porcine pepsin in neutral and alkaline solutions". Prol. Sci. 2: 1383–1390.

Chen, Z., Koelsch, G., Han, H.-P., Wang, X.-J., Lin, X., Hartsuck, J.A., and Tang, J. (1991) "Recombinant rhizopuspepsinogen", J. Biol. Chem. 266: 11718–11725.

Lin, Y,-Z., Fusek, M., Lin, X.L., Hartsuck, J.A., Kezdy, F.J., and Tang, J. (1992) "pH Dependence of kineticparameters of pepsin, rhizopuspepsin, and their active-site hydrogen bond mutants". J. Biol. Chem. 267: 18413–18418.

Lin, X.L., Liu, M.T., and Tang, J. (1992) "Heterologous expression of thermopsin, a heat stable acid proteinase". Enzyme Microb. Technol. 14: 696–701.

Lin, Y.-Z., Lin, X., Hong, L., Foundling, S., Heinrikson, R.L., Thaisrivongs, S., Leelamanit, W., Raterman, D., Shah, M., Dunn, B.M., and Tang, J. (1995) "Effect of point mutations on the kinetics and the inhibition of human immunodeficiency virus type 1 protease: relationship to drug resistance". Biochemistry 34: 1143–1152.

Ermolieff, J., Lin, X., and Tang, J. (1997) Kinetic properties of saquinavir-resistant mutants of human immunodeficiency virus type 1 protease and their implications in drug resistance in vivo. Biochemistry 36: 12364–12370.

Lin, X., Tang, J., Koelsch, G., Monod, M., and Foundling, S. (1993) "Recombinant canditropsin, an extracellular aspartic protease from yeast Candida tropicalis". J. Biol. Chem. 268__20143–20147.

Koelsch, G., Tang, J., Monod, M., Foundling, S.I., Lin, X. (1998) "Primary substrate specificities of secreted aspartic proteases of Candida albicans". Adv. Exp. Med. Biol. 436: 335–333.

Wang, X., Lin, X., Lowy, J.A., Tang, J., Zhang, X.C. (1998) "Crystal structure of the catalytic domain of human plasmin complexed with streptokinase", Science. 281: 1662–1665.

Wang, X., Terzyan, S., Tang, J., Loy, J., Lin, X., and Zhang, X. (2000) "Human plasminogen catalytic domain undergoes a novel conformational change upon activation" J. Mol. Biol. (in press).

Faro, C., Ramalho-Santos, M., Vieira, M., Mendes, A., Simoes, I., Andrade, R., Verissimo, P., Lin, X., Tang, J., Pires, E. (1999) "Cloning and Characterization of cDNA Encoding Cardosin A, an RGD-containing Plant Aspartic Proteinase," J. Biol. Chem. 274 (40): 28724–28729.

Lin, X., Koelsch, G., Wu, S., Downs, D., Dashti, A., and Tang, J. (2000) "Human aspartic protease memapsin 2 cleaves the β-secretase site of β-amyloid precursor protein. Proc. Natl. Aca. Sci. 97(4): 1456–1460.

Ghosh, A.K., Shin, D., Downs, D., Koelsch, G., Lin, X., Ermolieff, J., Tang, J. (2000) "Design of potent inhibitors form human brain memapsin 2 (β-secretase)" J. Amer. Chem. Soc., 122: 3522–3523.

The present invention will be further understood by reference to the following non-limiting examples.

EXAMPLE 1

Preferred Method for Refolding Recombinant Proteins

A. Reagents:
ZB media: 10 g N-Z-Amine A, 5 g NaCl/L
LB media: 10 g Tryptone, 5 g Yeast extract, 10 g NaCl/L, pH 7.5
8 M urea: 8 M urea, 0.1 M TRIS™, 1 mM glycine, 1 mM EDTA, pH 10
TN buffer: 0.05 mM TRIS™, 0.15 M NaCl, pH 7.5

B. Expression of the Recombinant Protein:
1. Expression plasmids should be transfected into an appropriate host, such as the BL21(DE3) strain of *E. coli* and plated on ZB/Ampicillin plates, which selects for the desired recombinant organisms. A single colony from each construct is inoculated into 100 ml of ZB/ampicillin media and grown 16 hat 37° C.
2. Inoculate 20 ml of the overnight culture into 1 L of LB/ampicillin, and shake at 37° C. till $OD_{600}$ reaches 0.4–0.6. Add IPTG to 0.5 mM, then shake for 3 h.
3. Centrifuge and resuspend cells in 20 ml of TN/1% Triton™ X-100. Add 10 mg lysozyme and freeze at −20° C. overnight.
4. Thaw the frozen cells, add 20 μl 1 M $MgSO_4$ 100 μg DNAase, and stir until the bacterial DNA is completely dissolved.
5. Add 250 ml of TN/1% Triton and stir for 2–4 h. Centrifuge and repeat the Triton wash one more time.
6. Dissolve the pellet in 10 ml of 8 M urea solution, add beta-Mercaptoethanol to 100 mM. This solution can be ultracentrifuged, and is then ready for refolding.

C. Refolding and Purification:
The $OD_{280}$ of the solution containing the inclusion bodies is adjusted to 5.0 with the 8 M urea solution. The final solution contains the following reducing reagents:
10 mM beta-Mercaptoethanol
10 mM DTT (Dithiothreitol)
1 mM reduced glutathione (GSH)
0.1 mM oxidized glutathione (GSSG)
The final pH of the solution is 10.0.
1. The above solution is rapidly diluted into 20 volumes of 20 mM TRIS™ base, the pH is adjusted to 9.0, and then slowly adjusted to 8.0 with 1 M HCl, by adjusting pH to 8.8 for twenty four hours, then 8.6 for twenty four hours, etc., until the pH is 8.0. Alternatively, the proteins can be refolded using dialysis. The $OD_{280}$ of the 8 M urea solution is adjusted to 0.5, and dialyzed against 20 volumes of TRIS™ base. The pH of the solution is again slowly adjusted to 8.0.
2. The refolded material is then concentrated by ultrafiltration, and separated by gel filtration, for example, on a SEPHACRYL™ S-300 column equilibrated with 20 mM TRIS™, HCl, 0.4 M urea, pH 8.0.
3. The S-300 fractions can be checked by running a non-reduced SDS-PAGE. The wrongly refolded protein runs at a very high molecular weight, while folded proteins run at a normal molecular weight.
4. The refolded peak from the S-300 column can be further purified with a FPLC Resource-Q™ or Resource-S™ column, which is equilibrated with 20 mM TRIS™-HCl (HEPES buffer for Resource-S™), 0.4 M urea, pH 8.0. The enzyme is eluted from the column with a linear gradient of NaCl. Table I lists all of the proteins which have been refolded directly or as inclusion bodies.

EXAMPLE 2

Expression and Refolding of Memapsin 2

Pro-memapsin 2 was PCR amplified and cloned into the BamHI site of a pET11a vector. The resulting vector expresses pro-memapsin 2 having a sequence from Ala-8p to Ala 326. Two expression vectors, pET11-memapsin 2-T1 (hereafter T1) and pET11-memapsin 2-T2 (hereafter T2), were constructed. In both vectors, the N-terminal 15 residues of the expressed recombinant proteins are derived from the expression vector. Pro-memapsin 2 residues start at residue Ala-16. The two recombinant pro-memapsin 2s have different C-terminal lengths. Clone T1 ends at Thr-454 and clone T2 ends at Ala-419. The T1 construct contains a C-terminal extension from the T2 construct but does not express any of the predicted transmembrane domain.

The T1 and T2 expression vectors were separately transfected into *E. coli* strain BL21(DE3). The procedures for the culture of transfected bacteria, induction for synthesis of recombinant proteins and the recovery and washing of inclusion bodies containing recombinant proteins are essentially as described by Lin et al., 1994 Methods in Enzymology 214, 195–224. Basically, the inclusion bodies are washed with 1% (v/v) Triton X-100 and 0.15 M NaCl in 0.1 M Tris™ HCl, pH 7.4, the insoluble protein is dissolved in a solution containing 8 M urea, 0.05 M cyclohexylaminopropanesulfonic acid, 10 mM 2-mercaptoethanol, 10 mM DTT (Dithiothreitol), 1 mM reduced glutathione (GSH), 0.1 mM oxidized glutathione (GSSG), 1 mM glycine, and 1 mM ethylenediaminetetraacetic acid (EDTA), pH 10.5, to a protein concentration of about 5 mg/ml. This solution is added dropwise to 20 vol of rapidly stirred 20 mM Tris base. The pH of the diluted solution is readjusted to 9.0 with 1 M HCl and kept at 4° C. for 24 hr. The pH is than adjusted to 8.8 with 1 M HCl, and kept at 4° C. for 24 hr again. The process is repeated until the pH is adjusted to 8.0.

Three different refolding methods have produced satisfactory results.

(i) The Rapid Dilution Method.

Pro-memapsin 2 in 8 M urea/10 mM DTT (Dithiothreitol), 1 mM reduced glutathione (GSH), 0.1 mM oxidized glutathione (GSSG), with $OD_{280nm}=5$ was rapidly diluted into 20 volumes of 20 mM-Tris base. The solution was slowly adjusted into pH 8 with 1 M HCl. The refolding solution was then kept at 4° C. for 24 to 48 hours before proceeding with purification.

(ii) The Reverse Dialysis Method

An equal volume of 20 mM TRIS™, 0.5 mM oxidized/1.25 mM reduced glutathione, pH 9.0 is added to rapidly stirred pro-memapsin 2 in 8 M urea/10 mM beta-mercaptoethanol with $OD_{280nm}=5$. The process is repeated three more times with 1 hour intervals. The resulting solution is then dialyzed against sufficient volume of 20 mM TRIS™ base so that the final urea concentration is 0.4 M. The pH of the solution is then slowly adjusted to 8.0 with 1 M HCl.

iii. The Preferred Method for Refolding.

Inclusion bodies are dissolved in 8 M urea, 0.1 M TRIS™, 1 mM Glycine, 1 mM EDTA, 100 mM beta-mercaptoethanol, pH 10.0. The $OD_{280}$ of the inclusion bodies are adjusted to 5.0 with the 8 M urea solution without beta-mercaptoethanol. The final solution contains the following reducing reagents: 10 mM beta-mercaptoethanol, 10 mM DTT (Dithiothreitol), 1 mM reduced glutathione, and 0.1 M oxidized glutathione. The final pH of the solution is 10.0.

The above solution is rapidly diluted into 20 volumes of 20 mM TRIS™ base, the pH is adjusted to 9.0, and the resulting solution is kept at 4° C. for 16 hr. The solution is equilibrated to room temperature in 6 hr, and the pH is adjusted to 8.5. The solution is returned to 4° C. again for 18 hr.

The solution is again equilibrated to room temperature in 6 hr, and the pH is adjusted to 8.0. The solution is returned to 4° C. again for 4 to 7 days.

Purification of Recombinant Pro-Memapsin 2-T1

The refolded material is concentrated by ultrafiltration, and separated on a SEPHACRYL™ S-300 column equilibrated with 20 mM TRIS™ HCl, 0.4 M urea, pH 8.0. The refolded peak (second peak) from the S-300 column can be further purified with a FPLC RESOURCE-Q™ column, which is equilibrated with 20 mM TRIS™-HCl, 0.4 M urea, pH 8.0. The enzyme is eluted from the column with a linear gradient of NaCl. The refolded peak from S-300 can also be activated before further purification. For activation, the fractions are mixed with equal volume 0.2 M Sodium Acetate, 70% glycerol, pH 4.0. The mixture is incubated at 22° C. for 18 hr, and then dialyzed twice against 20 volumes of 20 mM Bis-TRIS™, 0.4 M urea, pH 6.0. The dialyzed materials are then further purified on a FPLC RESOURCE-Q™ column equilibrated with 20 Bis-TRIS™, 0.4 M urea, pH 6.0. The enzyme is eluted with a linear gradient of NaCl.

Modifications and variation of these methods are intended to come within the scope of the appended claims.

I claim:

1. A method for refolding of a recombinant protein comprising
    maintaining the protein at a pH of 9.0 or greater, in the presence of one or more chaotrophic and reducing agents, and
    decreasing the pH of the solution gradually over a period of at least about 24 hrs to pH about 8.0 to induce renaturation of the protein so that it qualitatively exhibits a biological activity and structural characteristic of the protein.

2. The method of claim 1 wherein the pH is decreased in increments equivalent to 0.2 pH units per 24 hours.

3. The method of claim 1 wherein the protein is maintained at a pH of greater than 9.0 for a period of at least 24 hours.

4. The method of claim 1 wherein the pH is decreased by addition of acid.

5. The method of claim 1 wherein the pH is decreased by dilution or dialysis into a solution of a lower pH.

6. The method of claim 1 wherein the chaotrophic and reducing agents are selected from the group consisting of between 0.5 and 1.0 M urea, 0.1 mM to 100mM beta-mercaptoethanol, 0.1 mM to 100 mM DTT, 0.1 mM to 10 mM reduced glutathione, and 0.1 mM to 10 mM oxidized glutathione.

7. The method of claim 1 wherein the protein is first extracted from bacterial inclusion bodies.

8. The method of claim 7 wherein the bacteria is *E. coli*.

9. The method of claim 7 wherein the inclusion bodies are dissolved at a final pH of between 9 and 10.

10. The method of claim 1, wherein the protein is maintained at a pH above about 10.0.

11. The method of claim 1, wherein the protein is maintained at a pH above about 11.0.

12. The method of claim 1, wherein the protein is maintained at a pH above about 12.0.

13. The method of claim 1 wherein the pH is decreased over a period of at least about 36 hours.

14. The method of claim 1, wherein the pH of the solution is reduced more quickly at the higher pH and more gradually nearer the pH about 8.0.

15. The method of claim 1 comprising the additional step of separating protein species which exhibits biological activity from inactive, or wrongly folded, protein species.

16. The method of claim 1 wherein the chaotrophic agent is urea.

17. The method of claim 1 wherein the chaotrophic agent is guanidine hydrochloride.

18. The method of claim 1 wherein the chaotrophic agent is L-arginine.

19. The method of claim 1 wherein the reducing agent is dithiothreitol (DTT).

20. The method of claim 1 wherein the reducing agent is β-mercaptoethanol.

21. The method of claim 1 wherein the reducing agent is a combination of reduced glutathione (GSH) and oxidized glutathione (GSSG).

22. The method of claim 7 wherein the inclusion bodies are dissolved at a final pH of greater than 9.0.

23. The method of claim 7 wherein the inclusion bodies are dissolved at a final pH of greater than 10.0.

24. The method of claim 7 wherein the inclusion bodies are dissolved in a solution containing 8 M urea, 0.1 M Tris, 1 mM glycine, 1 mM EDTA, 10 mM beta-mercaptoethanol, 10 mM dithiothreitol, 1 mM reduced glutathione, 0.1 mM oxidized glutathione, pH 10.

25. The method of claim 24 further comprising adjusting absorbance at 280 nm of the solution to 5.0; and rapidly diluting the solution into 20 volumes of 20 mM Tris base before the step of decreasing the pH of the solution.

* * * * *